US007778844B2

(12) United States Patent
Ammer et al.

(10) Patent No.: US 7,778,844 B2
(45) Date of Patent: Aug. 17, 2010

(54) SYSTEM AND METHOD FOR MANAGING THE EXCHANGE OF INFORMATION BETWEEN HEALTHCARE SYSTEMS

(75) Inventors: Mary J. Ammer, Roseville, MN (US); Deborah J. Belcher, Hinesburg, VT (US); Monique Harold, Haymarket, VA (US); Esther Khoury, Greensboro, NC (US)

(73) Assignee: IDX Investment Corporation, South Burlington, VT (US)

( * ) Notice: Subject to any disclaimer, the term of this patent is extended or adjusted under 35 U.S.C. 154(b) by 1233 days.

(21) Appl. No.: 11/196,875

(22) Filed: Aug. 4, 2005

(65) Prior Publication Data

US 2007/0033066 A1 Feb. 8, 2007

(51) Int. Cl.
*G06Q 10/00* (2006.01)
*G06Q 50/00* (2006.01)

(52) U.S. Cl. .......................................... 705/2
(58) Field of Classification Search ............. 705/2, 705/3, 4
See application file for complete search history.

(56) References Cited

U.S. PATENT DOCUMENTS

| 4,491,725 | A | 1/1985 | Pritchard |
| 4,667,292 | A | 5/1987 | Mohlenbrock et al. |
| 4,686,624 | A | 8/1987 | Blum et al. |
| 4,857,716 | A | 8/1989 | Gombrich et al. |
| 4,858,121 | A | 8/1989 | Barber et al. |
| 5,225,976 | A | 7/1993 | Tawil |
| 5,359,509 | A | 10/1994 | Little et al. |
| 5,412,756 | A | 5/1995 | Bauman et al. |
| 5,504,674 | A | 4/1996 | Chen et al. |
| 5,550,734 | A | 8/1996 | Tarter et al. |
| 5,890,129 | A | 3/1999 | Spureon |
| 5,915,241 | A | 6/1999 | Giannini |
| 6,003,007 | A | 12/1999 | DiRienzo |
| 6,076,066 | A | 6/2000 | DiRienzo et al. |
| 6,088,677 | A | 7/2000 | Spureon |
| 6,196,970 | B1 | 3/2001 | Brown |
| 6,283,761 | B1 | 9/2001 | Joao |
| 6,343,271 | B1 | 1/2002 | Peterson et al. ............... 705/4 |
| 6,343,310 | B1 | 1/2002 | DiRienzo |
| 6,714,913 | B2 * | 3/2004 | Brandt et al. ................. 705/2 |
| 7,039,593 | B2 | 5/2006 | Sager |
| 7,072,863 | B1 | 7/2006 | Phillips et al. |
| 7,222,079 | B1 | 5/2007 | Seare et al. |

(Continued)

OTHER PUBLICATIONS

"LOINC, a Universal Standard for Identifying Laboratory Observations: A 5-Year Update"; Clinical Chemistry: vol. 49, pp. 624-633; 2003.*

(Continued)

*Primary Examiner*—Gerald J. O'Connor
*Assistant Examiner*—John A Pauls
(74) *Attorney, Agent, or Firm*—Andrus, Sceales, Starke & Sawall, LLP

(57) ABSTRACT

An improved system for managing the exchange of information between healthcare systems. The system automatedly processes a healthcare data inquiry to produce a response readable by a requestor. This response may include content data, such as claims attachment data requested in a healthcare claims attachment inquiry. The content data may reside on data stores which the system must access in order to retrieve the necessary content data. The system may use criteria for automatedly interpreting the healthcare data inquiry.

29 Claims, 9 Drawing Sheets

U.S. PATENT DOCUMENTS

| | | |
|---|---|---|
| 7,415,431 B2 | 8/2008 | Pintsov |
| 7,490,048 B2 | 2/2009 | Joao |
| 2002/0019749 A1 | 2/2002 | Becker et al. |
| 2002/0032583 A1* | 3/2002 | Joao .............................. 705/2 |
| 2002/0062229 A1 | 5/2002 | Alban et al. |
| 2002/0077849 A1 | 6/2002 | Baruch et al. |
| 2002/0077869 A1 | 6/2002 | Doyle et al. |
| 2002/0120464 A1 | 8/2002 | Kirk |
| 2002/0173992 A1 | 11/2002 | Dang |
| 2002/0194029 A1 | 12/2002 | Guan et al. |
| 2002/0198739 A1* | 12/2002 | Lau et al. ....................... 705/3 |
| 2003/0028404 A1 | 2/2003 | Herron et al. |
| 2003/0074248 A1 | 4/2003 | Braud et al. |
| 2003/0078812 A1 | 4/2003 | Uchikubo |
| 2003/0078813 A1* | 4/2003 | Haskell et al. ................. 705/3 |
| 2003/0083903 A1 | 5/2003 | Myers |
| 2003/0187695 A1 | 10/2003 | Drennan |
| 2003/0191665 A1 | 10/2003 | Fitzgerald et al. |
| 2003/0200119 A1 | 10/2003 | Lewis et al. |
| 2004/0205664 A1 | 10/2004 | Prendergast |
| 2004/0249677 A1* | 12/2004 | Datta et al. .................... 705/3 |
| 2005/0251429 A1 | 11/2005 | Ammer et al. |
| 2006/0064313 A1 | 3/2006 | Steinbarth et al. |
| 2007/0027718 A1 | 2/2007 | Amerantes et al. |

OTHER PUBLICATIONS

"Empire Medicare Services Claims Attachment Pilot Project Overview"; WEDI Claim Attachment Pilot Advisory Committee; Nov. 10, 2004.*

"Demystifying the Health Care Claim Attachment" (Powerpoint Presentation); Gary Beatty; The Tenth National HIPAA Summit; Apr. 7, 2005.*

Office Action, USPTO, U.S. Appl. No. 11/748,611, Mar. 4, 2009.

"*XML-Based Claims Attachments Business Benefits,*" by W. Rishel, Technology, T-20-2117, Aug. 28, 2003.

"*XML-Based Claims Attachments Technical Tutorial,*" by W. Rishel, Tutorials, TU-20-2112, Aug. 28, 2003.

"*HIPAA and Claims Attachments, Preparing for Regulation,*" by the Attachments Special Interest Group (ASIG) at Health Level Seven (HL7), 2003-2004 Health Level Seven, Inc., Sep. 30, 2003 (Editor's note May 2004).

* cited by examiner

FIG. 6

SYSTEM AND METHOD FOR MANAGING THE EXCHANGE OF INFORMATION BETWEEN HEALTHCARE SYSTEMS

FIELD OF THE INVENTION

The present invention generally relates to the field of healthcare administration. In particular, the present invention is directed to an improved system and method for managing the exchange of information between healthcare systems.

BACKGROUND OF THE INVENTION

The healthcare industry consists of a wide network of interrelated systems that use a number of complex processes for exchanging information. This network consists of physicians, hospitals, clinics, laboratories, insurance plans, and other ancillary services and plans. These individual components further include individual departments specialized in managing a vast array of patient information. This information often resides in any number of forms and in any number of locations. Thus, a particular exchange between two parties may become a complicated and inefficient process resulting in a substantial waste of resources, time, and money.

The adjudication of healthcare claims is one example of these complicated information exchange processes. This often slow-moving procedure involves two parties, the health plans, e.g., insurance plans, and care delivery organizations (CDOs), e.g. hospitals and physicians, that unfortunately conduct business in a manner that is frequently adverse. Their relationship involves the adjudication of healthcare claims by the health plans and then payment to the CDOs for services rendered.

The adversarial nature of this relationship exists in part due to animosity over the claims attachment process. This process, illustrated generally in FIG. 1, typically starts, as indicated at step 10, when a healthcare claim enters the health plan adjudication process. The health plan then determines, at step 20, whether additional information is necessary to complete the adjudication of the healthcare claim. The decision that the healthcare claim contains all relevant information prompts the health plan to pay the provider, as indicated at step 30. An adverse determination, however, prompts the health plan to send an inquiry, at step 40, to the CDO requesting additional documentation. The CDO must fulfill the inquiry, step 50, by locating, assembling, and forwarding the requested documentation back to the health plan. The health plan continues adjudication, and may repeat this procedure several times for a single healthcare claim. As a result, CDOs may respond to claims attachment inquiries with large amounts of unnecessary documentation in an effort to stave off any additional documentation requests for a specific claim.

This often burdensome response is made worse by the healthcare industry's continued reliance on paper documents and scanned images for fulfilling most attachment requests. This reliance results in substantial administrative costs in connection with resources, adjudication time, and manual labor necessary for processing and responding to the claims attachment inquiries. The federal government responded to these issues by mandating, in the Health Insurance Portability and Accountability Act (HIPAA) of 1996, the use of electronic data interchange standards for the electronic conveyance of healthcare data. This mandate aims to make the process of submitting and adjudicating healthcare claims more efficient by providing a structured set of standardized electronic data to payers. The structured data will lower administrative overhead by reducing the pervasive need for human intervention for reviewing every healthcare claims attachment inquiry. These changes will improve turnaround time and provide a level of predictability. The goal, of course, is to improve the flexibility of the entire system and ultimately lower the cost of delivering healthcare services.

The application of the HIPAA standards to the claims attachment process, discussed previously and illustrated in FIG. 1, is generally illustrated in FIG. 2. As shown, HIPAA mandates the use of standard X12N formats for the exchange of data between the health plans and CDOs. The health plans will request additional documentation using X12N 277 Request for Additional Information (277 Request) transactions. The CDOs receive these transactions and transmit to the health plan a X12N 275 Additional Information in Support of the Healthcare Claim or Encounter (275 Response).

The 275 Response contains the requested documentation in HL7 Clinical Document Architecture (CDA) format. The CDA format allows the exchange of healthcare documents through electronic data interchange networks and software tools by specifying the document structure. The CDA standard includes three variant formats that accommodate manual or auto-adjudication of healthcare claims. The manual adjudication, or "human decision-making," formats allow scanned images or free-form text to be electronically sent in the 275 Response and reviewed by the person adjudicating the healthcare claim. In contrast, the auto-adjudication, or "computer decision-making," format contains additional structured information that allows computer-based decision algorithms to extract the content data. The additional information includes Logical Observation Identifier Names and Codes (LOINC) codes, a universal code for identifying and reporting clinical and laboratory observations in HL7 electronic messages.

Adoption of auto-adjudication by health plans and CDOs has been stymied by a lack of comprehensive systems for processing claims attachment inquiries. These entities stand to benefit from computer-based systems that simplify the exchange of information. A simplified data exchange process would lower health plan administrative overhead by reducing human adjudication. This reduction would facilitate the adjudication of claims and ultimately provide more timely payment to CDOs. These benefits, however, could additionally be realized throughout a number of other healthcare systems that rely extensively on information exchange to complete healthcare business transactions.

SUMMARY OF THE INVENTION

In one aspect, the present invention provides a system for handling one or more healthcare data inquiries that require content data. The system generally includes a processing module for receiving one or more healthcare data inquiries, in a standard healthcare format, that request one or more desired content data. The processing module may communicate with a worklist module for storing one or more work items and a response module for sending the desired content data to a requester in a standard healthcare data format.

In another aspect, the present invention provides a system for responding to a healthcare data inquiry for content data from one or more data stores. The system generally includes a rules module that has one or more criteria for interpreting various healthcare data inquiries. The rules module may communicate with a processing module that compares a healthcare data inquiry, with one or more desired content data, to one or more criteria to identify the data elements associated with the healthcare data inquiry. The processing module may also retrieve the data elements from the data stores. A response module, communicating with the processing module, sends the data elements to a requestor in a standard healthcare inquiry format.

In still another aspect, the present invention provides a system for automatically retrieving desired content data for a healthcare claim from one or more data stores. The system generally includes a receiver module for receiving a healthcare data inquiry, including a request for desired content data, from a requestor and a rules module having one or more criteria for interpreting for interpreting various healthcare data inquiries. The rules module may communicate with a comparison module that compares the healthcare data inquiry to the rules to determine one or more data elements associated with the request and to determine the location of the data stores that include those data elements. An acquisition module, communicating with the comparison module, retrieves the one or more data elements and a response module sends the one or more data elements to the requestor in a standard format.

In another aspect, the present invention provides a method for responding to a healthcare data inquiry. The method generally includes the following steps: receiving a healthcare data inquiry, including a request for one or more content data, from a requestor; automatedly determining one or more data elements associated with the request by using a criteria with one or more rules for interpreting a variety of content data; automatedly determining a location of the one or more data elements amongst one or more data stores; retrieving the one or more data elements from the one or more data stores; formatting the one or more data elements into a claims attachment in a predetermined format; and transmitting the claims attachment to a requester.

In yet another aspect, the present invention provides a system for automatically modifying a claims financial system. The system generally includes a management module for processing a plurality of healthcare data inquiries from a requester. The management module communicates with a statistics module for collecting statistics associated with the plurality of healthcare data inquiries. An intelligent learning module communicates with the statistics module and analyzes the statistics and modifies the one or more claims creation rules of a claims financial system.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein:

FIG. 6 is a screen shot of a graphical user interface used in at least one embodiment of the present invention;

DETAILED DESCRIPTION

Presently, systems for handling healthcare data inquiries relating to healthcare systems employ manual participation and paper records to a significant extent. These systems often involve a healthcare provider and a third party payer exchanging paper documents to complete a healthcare claims payment process. These manual systems continue existing because present processing solutions fail to provide a comprehensive scheme for efficiently processing healthcare data inquiries.

Figure 1:
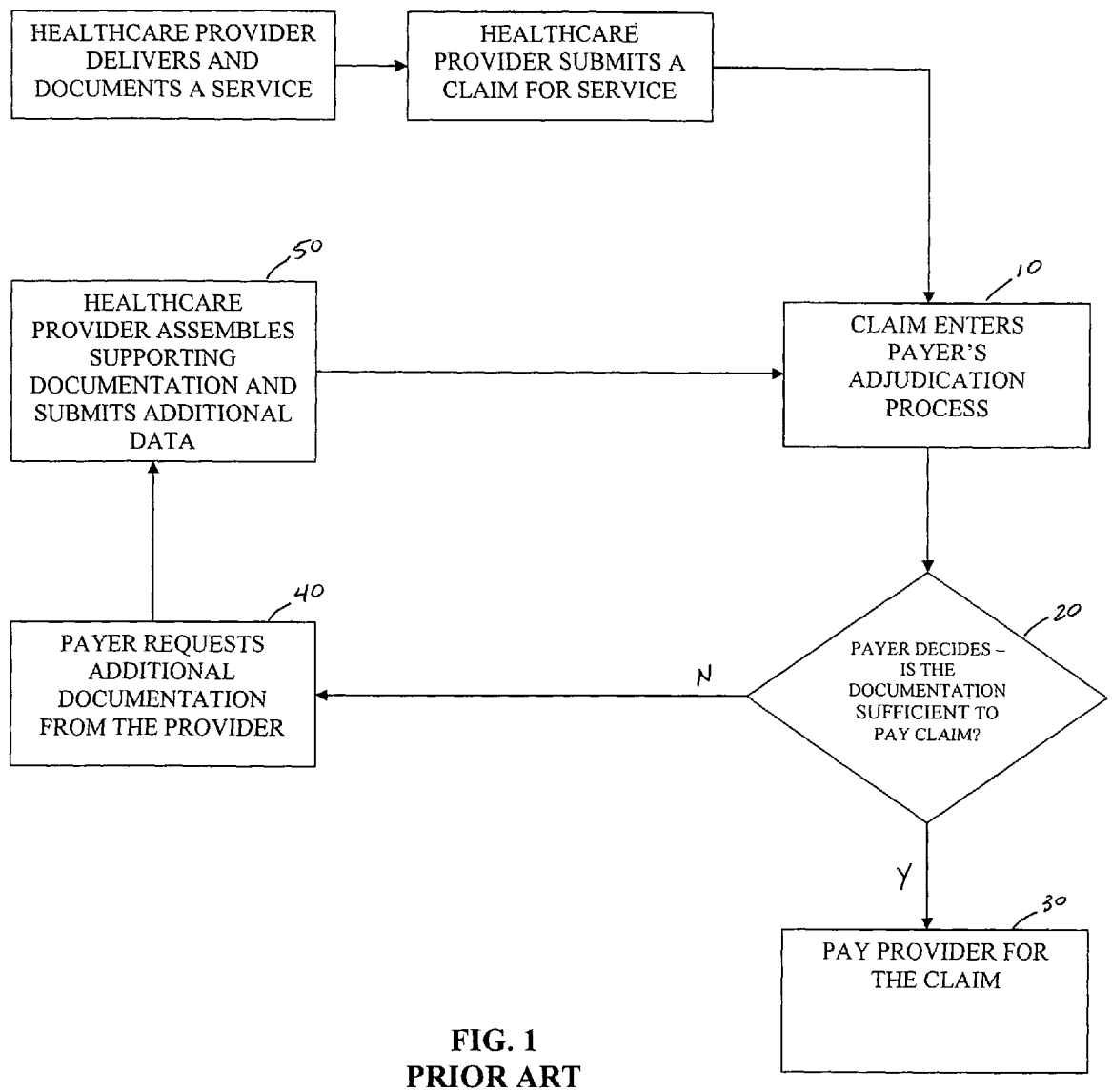
FIG. 1 is a block diagram showing a known healthcare data inquiry process for completing a healthcare claims attachment transaction.
Figure 2:
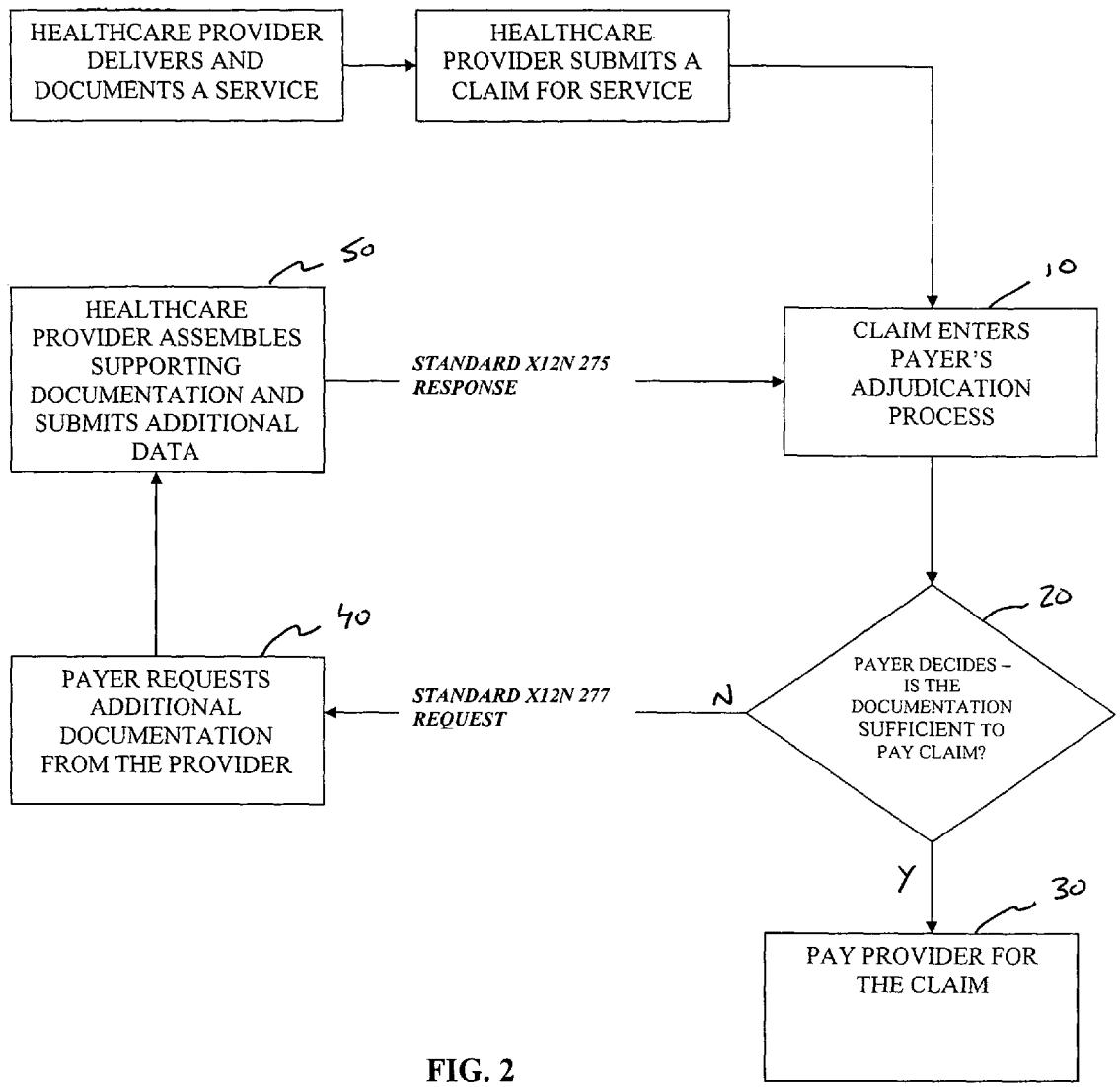
FIG. 2 is a block diagram showing how the healthcare data inquiry process of FIG. 1 could be implemented using standard electronic transactions for completing a healthcare claims attachment transaction.

In contrast, the present invention is directed to an improved system and method of managing and processing healthcare data inquiries. These inquiries include, but are not limited to, requests for clinical information related to claims adjudication, claim appeals, utilization review, subrogation claims, legal matters, audits, healthcare referral, and service authorization. As discussed previously, FIG. 2 generally illustrates an example of a document exchange between a healthcare provider and third party payer during a claim adjudication. This exchange utilizes standard electronic document formats meant to expedite the adjudication by streamlining the healthcare data inquiry. Likewise, an embodiment of the present invention, as discussed in more detail below, exploits these standardized formats by automatedly enhancing the handling of the healthcare data inquiry. It should be understood that the present invention is not limited to this (or any other) particular embodiment of the invention, but rather is intended to cover all systems and methods that fairly fall within the broad scope of the appended claims.

Figure 3:
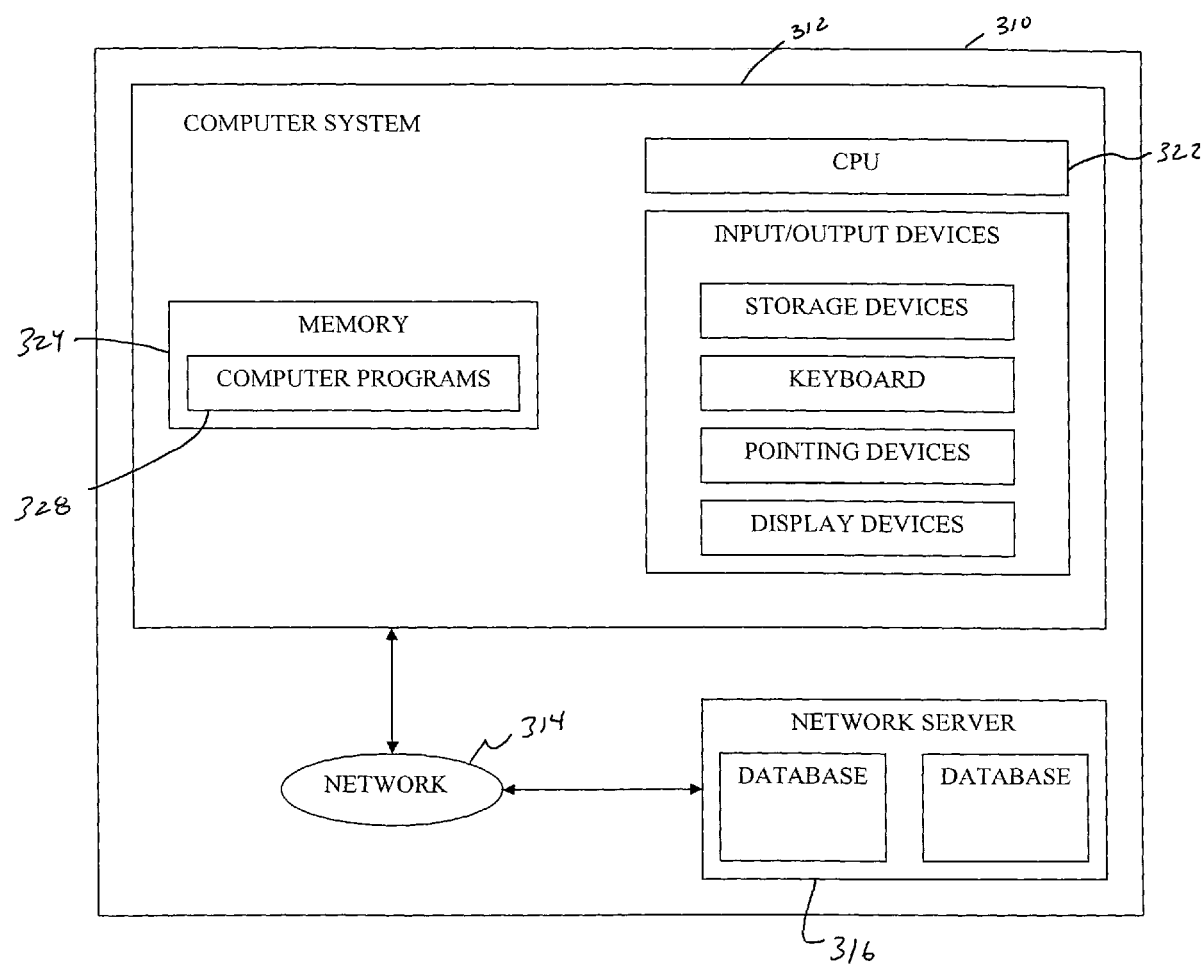
FIG. 3 is a block diagram showing an embodiment of the present invention for managing the exchange of information between healthcare systems as implemented in an appropriate computing environment.

Referring again to the drawings, wherein like reference numerals refer to like elements, FIG. 3 illustrates an example of a system 310 of the present invention. Although not required, the invention will be described generally in terms of computer-executable instructions, such as program modules, that are executed by a conventional, general purpose, digital computer. Typically, program modules include routines, programs, objects, components, data structures, etc. that perform specific tasks. The invention may be practiced with a variety of computer system configurations, including networked client-server computing systems, hand-held devices, programmable consumer electronics, minicomputers, mainframe computers, and the like. The invention will typically, but not necessarily, be practiced in distributed computing environments where tasks are performed by remote processing devices that are linked through a communications network, e.g. a LAN, WAN or an Internet-based network. In a distributed computing environment, program modules may be located in both local and remote memory storage devices.

It is contemplated that the system of the present invention will operate in a networked computing environment including a computer system 312 that is connected, directly or indirectly via network 314 (e.g., a LAN, WAN, or Internet), to one or more network servers 316. In some cases, a computer system 312 may include multiple computer systems 312 operably connected via a LAN, WAN or the Internet. Computer system 312 includes a computer central processing unit (CPU) 322, a computer memory 324, and input/output devices 326. System 310 includes computer programs 328 which, when executed by computing resources within system 310, provide system 310 the functionality of the present invention, as described in detail below.

Figure 4:
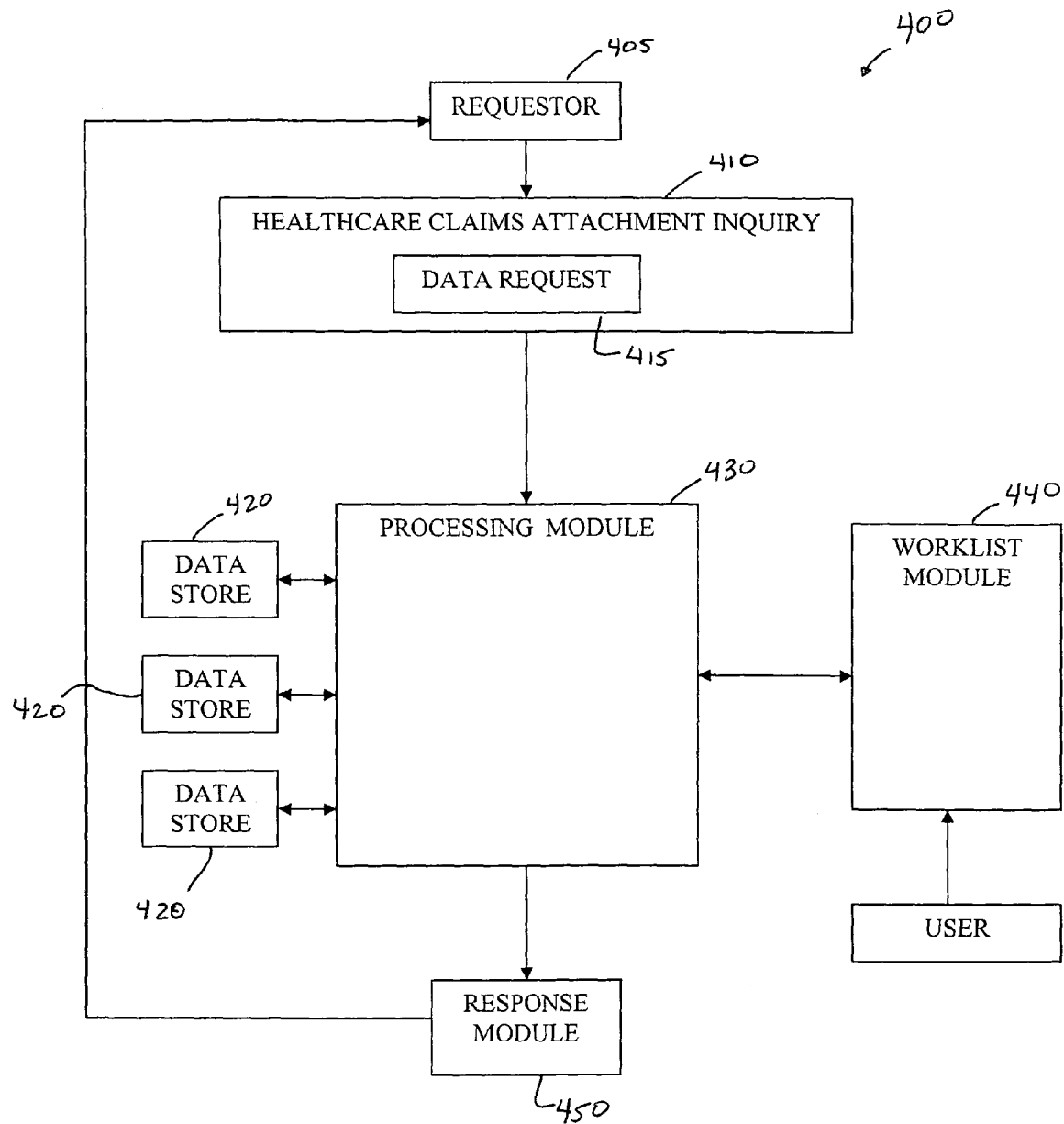
FIG. 4 is a block diagram showing an embodiment of the present invention for managing the exchange of information between healthcare systems.

Typically, a healthcare system requires an individual, usually a low to moderate skill-set office worker, to manually retrieve content data in response to a healthcare data inquiry. The office worker must frequently print, package, and send the content data to a healthcare plan for consideration. These time-consuming steps burden healthcare administrative resources by increasing costs and processing time. Accordingly, FIG. 4 illustrates a generalized embodiment of the present invention that limits significantly the extent of this individual intervention. The present invention is described below in more detail in connection with the embodiments of FIGS. 7 and 8. The embodiment of FIG. 4 includes a healthcare system 400 for processing healthcare data inquiries that may be implemented, for example, in the computing environment illustrated in FIG. 3.

These healthcare data inquiries may be submitted by one or more requesters 405. Requestor 405 may include, but is not limited to, a third party payer, a healthcare provider, a healthcare administrative system, a utilization review organization, a healthcare management organization, an electronic data interchange system, an internal processing activity, a manually initiated request, and any combination thereof. In addition, requestor 405 may also be a healthcare financial system adequately modified such that healthcare system 400 may be used to automatedly update the financial system records.

These entities typically transmit electronic healthcare data inquiries in a standard format. An example of a standard healthcare data inquiry is the X12N 277 Electronic Data Interchange ("EDI") format. A person of ordinary skill in the art, however, will understand from the present invention that requestor 405 may use other formats, including, but not limited to, a standard X12N 278 Healthcare Services Review Request, a standard X12N 278 Healthcare Services Review Response, a standard X12N 278 Healthcare Services Review Notification, and Web-based direct data entry ("DDE") alternatives.

Figure 5:
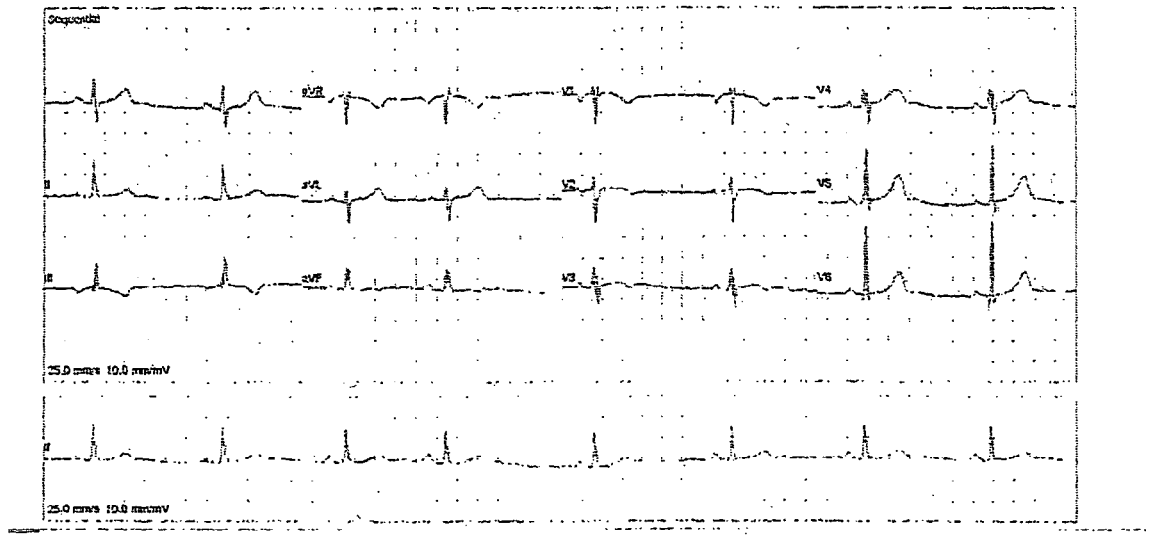
FIG. 5 is a screen shot of an example of information processed by an embodiment of the present invention.

An example of a healthcare data inquiry is a healthcare claims attachment inquiry 410, having one or more data requests 415. Data requests 415 may list information including, but not limited to, document type, patient identification, relevant healthcare providers, document status, and any combination thereof. The one or more data requests 415 may specify content data relating to, but not limited to, clinical reports, ambulance services, emergency department services, lab results, medications, rehabilitation services, children's preventive services, home healthcare services, dental services, durable medical equipment services, and consent forms. Accordingly, a person of ordinary skill in the art will understand that, according to the present invention, content data may include any healthcare-related information stored and accessible in an electronic medium. For example, content data may include, but is not limited to, the EKG report illustrated in FIG. 5. This content data may be located on one or more data stores 420, which may be databases residing on a network server 316 (FIG. 3). These databases may include, but are not limited to, clinical record systems, document imaging systems, direct data entry systems, and any combination thereof.

A processing module 430, operably connected to data stores 420, may accept healthcare claims attachment inquiries 410 from requesters 405. Processing module 430 may perform various operations that facilitate a response, and is adapted, via appropriate programming known to those skilled in the art, to receive a healthcare claims attachment inquiry 410 from any requester 405, including those listed above. These operations, described in more detail below, may automatedly attach content data, or content data locations, to healthcare claims attachment inquiry 410 for transmission back to requestor 405. In another embodiment, some healthcare claims attachment inquiries may be routed to a worklist module 440. This module provides a user access to healthcare claims attachment 410 to semi-automatedly attach content data, or content data locations, to healthcare claims attachment inquiry 410. In either embodiment, the acquired content data, or content data locations, may be converted into a standard format, such as HL7 CDA XML format, and routed to a response module 450. This module may complete the transaction by structuring healthcare claims attachment inquiry 410 into a standard response format, such as a X12N 275 EDI format, and transmitting the response to requester 405.

Figure 7:
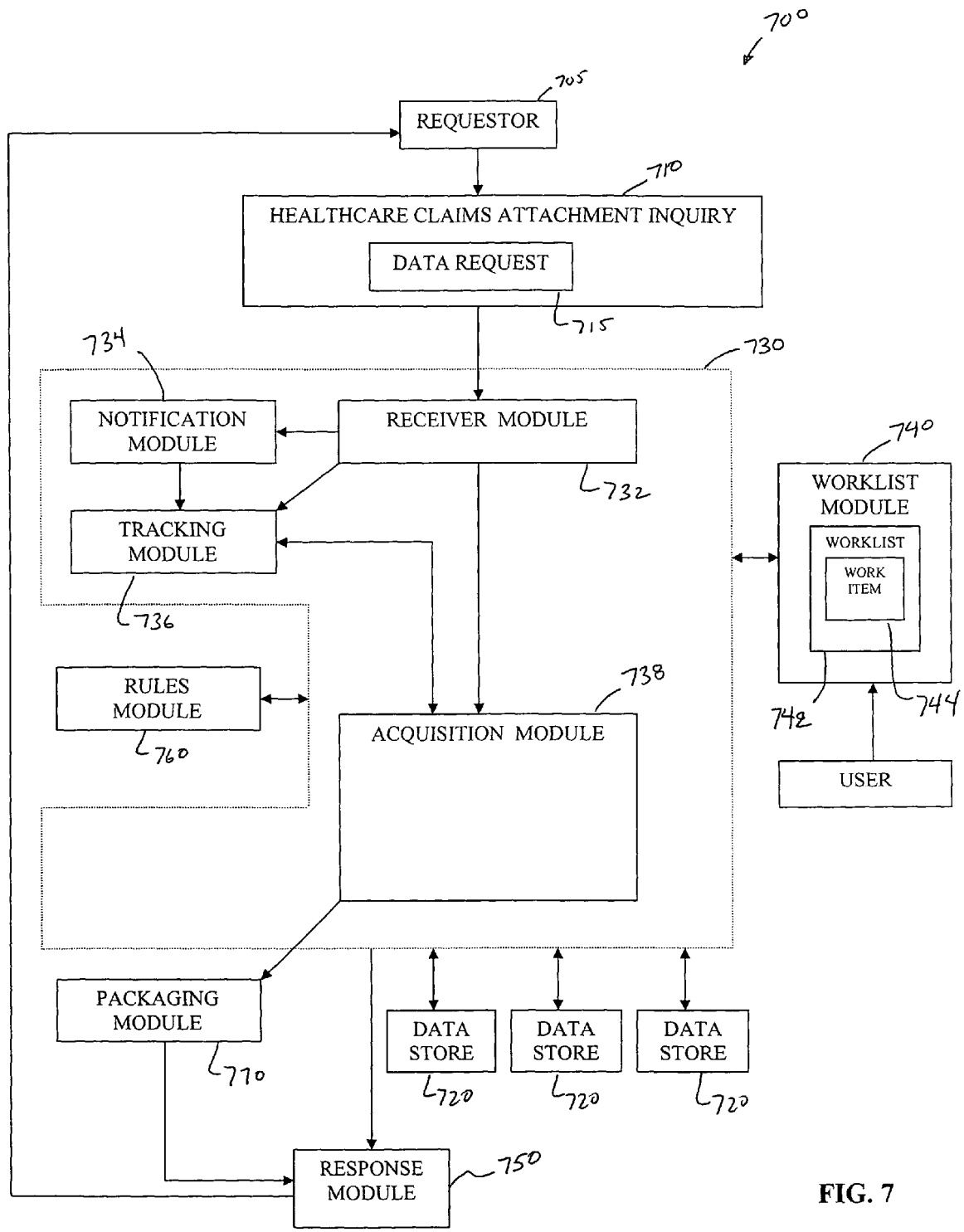
FIG. 7 is a block diagram showing an embodiment of the present invention for managing the exchange of information between healthcare systems.

Referring next to FIG. 7, a healthcare system 700 for handling healthcare data inquiries, such as healthcare claims attachment inquiries, is illustrated. This system provides a convenient semi-automated alternative for applying the standardized claims attachment process discussed previously, and illustrated generally in FIG. 2. Presently, the standardized process in FIG. 2 requires extensive manual intervention to successfully orchestrate a response to a healthcare claims attachment inquiry.

In contrast, healthcare system 700 improves this process by handling, from a requestor 705, one or more healthcare claims attachment inquiries 710 having one or more data requests 715. Data request 715 typically request content data located on one or more data stores 720. In one embodiment, healthcare system 700 uses a processing module 730, as discussed briefly above, to operate on each healthcare claim attachment inquiry 710. Processing module 730 may have various modules to aid in completing the healthcare claims attachment transaction. For example, processing module 730 may include a receiver module 732, that is adapted, via appropriate programming known to those skilled in the art, to receive a healthcare claims attachment inquiry 710 from any requester 705, including those discussed previously. Receiver module 732 may determine the identity of requestor 705 by examining the contents of healthcare claims attachment inquiry 710. This identity, or alternatively the entire healthcare claims attachment inquiry 710, may be routed to a notification module 734. In the latter case, notification module 734, instead of receiver module 732, may determine the identify of requestor 705.

Once identified, requestor 705 may receive a notification message from notification module 734. The notification message may be transmitted by way of an electronic message, electronic data transmission, web service, direct connection, and any combination thereof. In another embodiment, notification module 734 may be operably connected with a billing system. Notification module 734 may use this connection to automatedly update the healthcare claim or billing system corresponding to healthcare claim attachment inquiry 710.

Receiver module 732 or, alternatively notification module 734, may route healthcare claims attachment inquiry 710 to a tracking module 736. Tracking module 736 may store one or more healthcare claims attachment inquiry 710 and assign each a tracking identifier. The tracking identifier may consist of any identifying numeral, letter, or other symbol used to uniquely identify a healthcare claims attachment inquiry 710. The unique identification permits tracking module 736 to monitor healthcare claims attachment inquiries 710. For example, tracking module 736 may monitor the length of time that one or more healthcare claims attachment inquiries 710 are stored. In another example, tracking module 736 may monitor any delays in receiving content data from one or more data store 720. In these instances, an alert may be communicated to healthcare system 700 when the length of time has reached a critical point. This alert may prompt healthcare system 700 to respond to one or more healthcare claims attachment inquiries 710.

The response may involve processing module 730, through an acquisition module 738, working in conjunction with a worklist module 740, response module 750 and a rules module 760. Worklist module 740 develops one or more worklist 742 having one or more work items 744. In accordance with the present invention, processing module 730 may retrieve one or more data requests 715 from healthcare claims attachment inquiry 710. Each data request 715 may contain an identifying symbol used to identify one or more worklists 742 where data request 715 should reside. This selection may use an identifying symbol that specifies the type of content data requested. This type of identifying symbol includes, but is not limited to a clinical system code such as a Logical Observation Identifiers Names and Codes (LOINC) code, used for the electronic exchange of clinical information.

Processing module 730 may require specific instructions that enable the proper routing of data request 715 to an appropriate worklist 742. These instructions may reside within processing module 730. Alternatively, rules module 760 may have one or more criteria that describe an association between the identifying symbols and a corresponding worklist 742. Accordingly, processing module 730 may route each data request 715 to a corresponding worklist 742 by comparing the identifying symbols to the criteria of rules module 760. A match between the identifying symbol and the criteria may permit processing module 730 to correctly direct data request 715 to a worklist 744, where each data request 715 may be stored as one or more work items 744.

Figure 6:
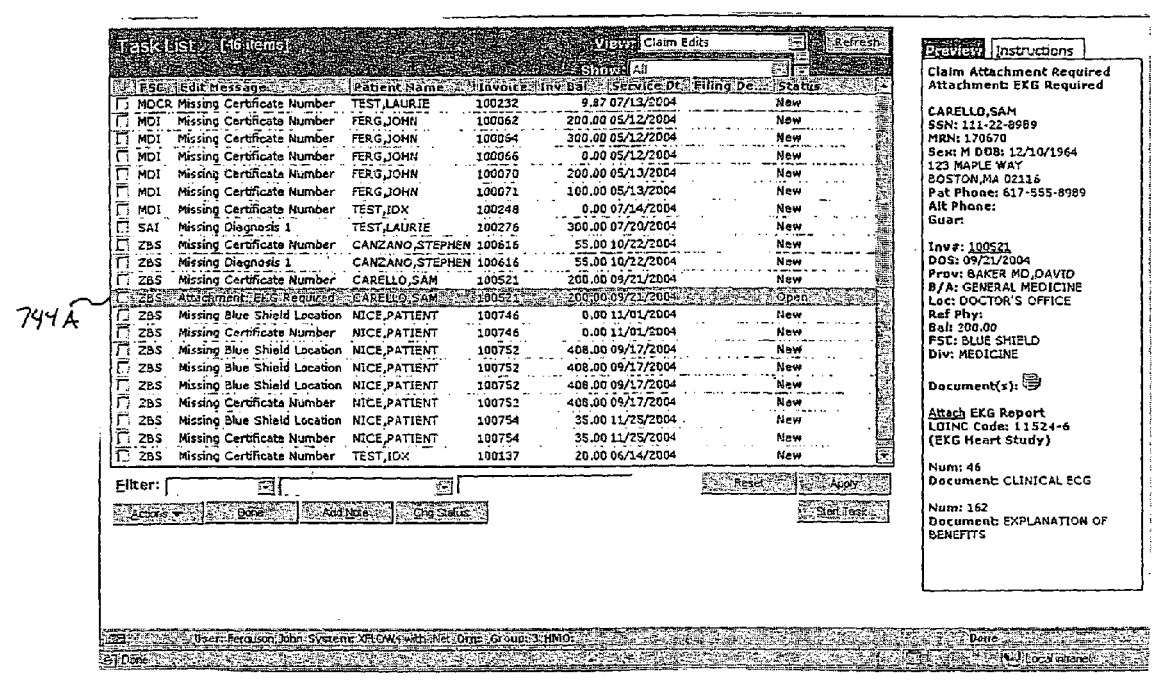

Each work item 744 typically contains all data associated with data request 715. Work items 744 may be stored and displayed in worklist 742, in the manner, for example, shown in FIG. 6. As an example, a work item 744A may be displayed on worklist 742 with the message "Attachment EKG Required", which indicates content data is required. A person of ordinary skill in the art, however, will understand that no standard format may be available, or required, for communicating with worklist module 740 or worklist 742.

Accordingly, a user might select one or more work items 744 and view information associated with data request 715. This information may include content data, such as scanned documents and text reports, necessary for the completion of the claims attachment transaction. Accordingly, the user may manually designate the content data, here the EKG of FIG. 5, for attachment to the claims attachment inquiry. The selection may prompt the corresponding data store 720 to notify processing module 730 that work item 744 is completed. This notification may be accompanied by the transmission of the content data, or content data location, to processing module 730.

After designation, work item 744 may be removed from worklist 742 or otherwise denoted in such a manner as to indicate the item as completed. An acquisition module 738 may convert the content data into a standard format, as described previously. This conversion prompts work item 744, with converted content data or with the content data location, to be routed to response module 750 for transmission to requester 705. In another embodiment, acquisition module 738 may be operably connected to tracking module 736. Acquisition module 738 may route healthcare claims attachment inquiry 710, with attached content data or with the location of the content data, to tracking module 736 for storage. Tracking module 736 may monitor one or more healthcare claims attachment inquiries 710, related to a single healthcare claim, until all healthcare claims attachment inquiries 710 have been fulfilled.

Acquisition module 738 and tracking module 736 may route healthcare claims attachment inquiries 710, with the content data or the content data location, to a response module 750. Response module 750, as discussed in previous embodiments, may complete the semi-automated process by transmitting healthcare claims attachment inquiry 710 to requester 705. The transmitted healthcare claims attachment inquiry 710 may be structured into a standard format, such as the X12N 275 EDI format discussed previously. In another aspect, response module 750 may combine a plurality of formatted healthcare claims attachment inquiry 710, associated with a single healthcare claim, and structure the plurality into a standard response for transmission to requestor 705.

Alternatively, the formatting of multiple healthcare claims attachment inquiries 710 may be completed by a packaging module 770. This module may provide an area where one or more healthcare claims attachment inquiries 710 may be routed. For example, a single healthcare claim may require a plurality of healthcare data inquiries 710 that may be routed from acquisition module 738 to packaging module 770. The plurality of healthcare claims attachment inquiries 710 may be packaged into a standard response format, as discussed previously, and forwarded to response module 750 for transmission to requestor 705. In another example, packaging module 770 may store one or more healthcare claims attachment inquires 710 related to a single healthcare claim. The completion of all inquiries related to the single healthcare claim will prompt packaging module 770 to format a standard response, and forward that response to response module 750. Response module 750 may update notification module 734, which may then automatedly notify the healthcare claim or billing system that the healthcare claims attachment transaction has been completed. Response module 750 may generate a response that includes, but is not limited to, the selected content data or selected content data location.

Figure 8:
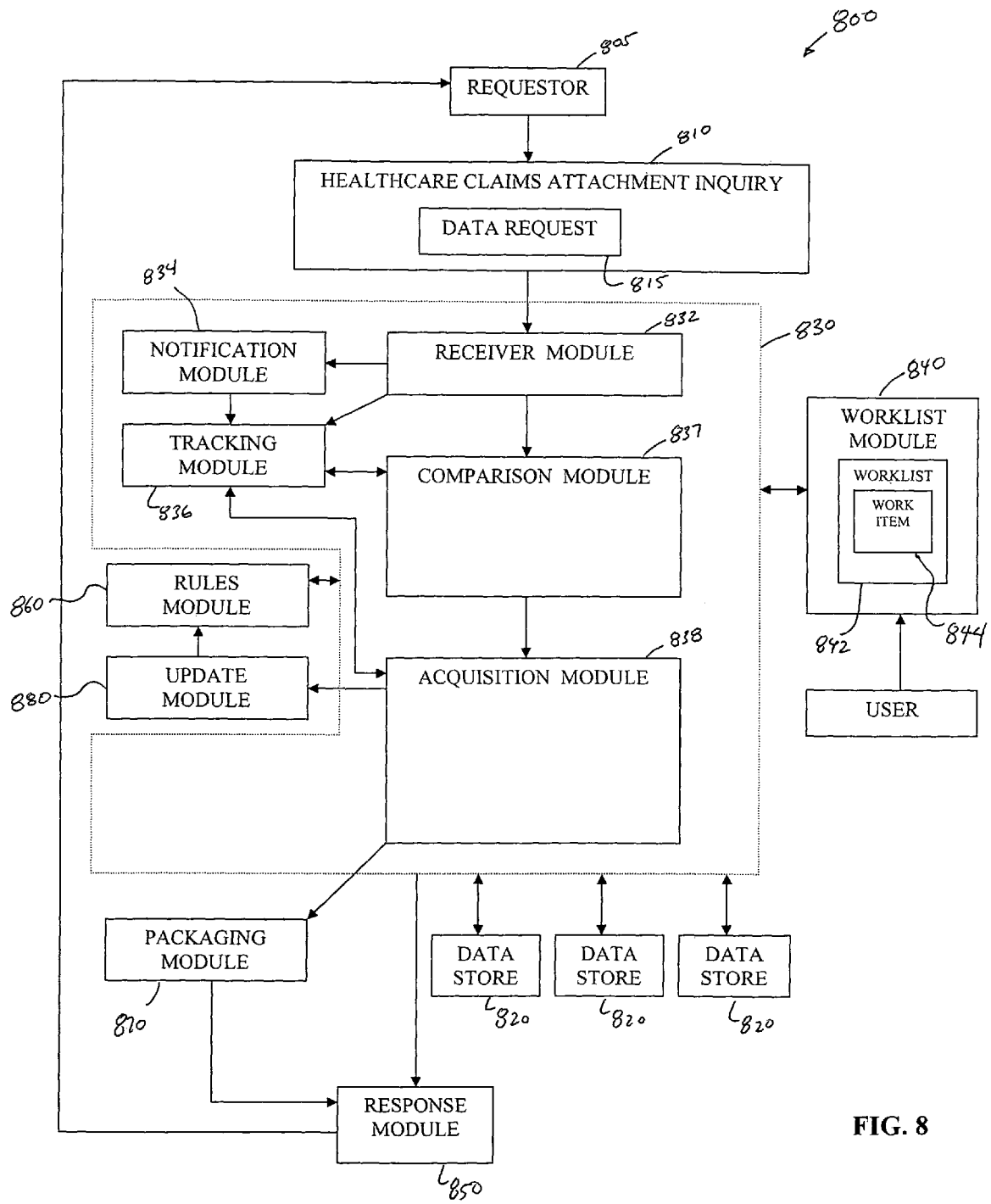
FIG. 8 is a block diagram showing an embodiment of the present invention for managing the exchange of information between healthcare systems.

To avoid the user involvement discussed above, another aspect of the present invention provides an automated system for dealing with healthcare data inquiries. Referring now to FIG. 8, healthcare system 800 automatedly locates and transmits content data, or content data locations, to a requestor 805. The transmission may be in response to one or more healthcare claims attachment inquiries 810 having one or more data requests 815. Each data request 815 may contain an identifying symbol, such as the LOINC codes discussed previously, that specifies the type of content data requested.

These identifying symbols may be used to locate content data stored on one or more data stores 820, which may be databases residing on a network server, as illustrated in FIG. 3. In accordance with the present invention, a processing module 830 may be operably connected to one or more data stores 820. This module, as described in detail above, operates on one or more healthcare claims attachment inquiries 810 from requestor 805. These operations may include receiving a healthcare claims attachment inquiry 810 through a receiver module 832 adapted, via appropriate programming known to those skilled in the art, to receive a healthcare claims attachment inquiry 410 from any requester 405, including those discussed previously. Further, processing module 830 may notify requester 805 using a notification module 834, and track the status of healthcare claims attachment inquiry 810 with a tracking module 836.

In addition to these features, processing module 830 may automatedly obtain the specified content data by translating the identifying symbol to determine the one or more data stores 820 having the requested content data. This translation, may require that processing module 830 use a comparison module 837 that retrieves one or more healthcare claims attachment inquiries 810 from tracking module 836. Comparison module 837 may operate on the retrieved healthcare claims attachment inquiry 810 to understand the content data necessary to complete the inquiry. These operations may include interpreting patient information, billing information, or other information unique to the specific healthcare claims attachment inquiry 810.

In one aspect, comparison module 837 may require specific instructions that enable a proper translation of the information within healthcare claims attachment inquiry 810. These instructions may reside within comparison module 837. Alternatively, the instructions may reside in a separate area, such as rules module 860, that is accessible to comparison module 837. Rules module 860, as discussed previously, may contain criteria that associate an identifying symbol, e.g., clinical system code, with identification information required to retrieve the requested content data. Comparison module 837 may compare healthcare claims attachment inquiry 810 to these criteria to attach the requested content data to healthcare claims attachment inquiry 810.

For example, comparison module 837 may recognize an identifying symbol corresponding to one or more healthcare claims attachment inquiry 810. The identifying symbol may be compared to the criteria of rules module 860. A match between the identifying symbol and the criteria may prompt comparison module 837 to copy the corresponding identification information to healthcare claims attachment inquiry 810. In another example, comparison module 837 may route healthcare claims attachment inquiry 810 to rules module 860. Rules module 860 may compare the identifying symbol to the stored criteria, amend healthcare claims attachment inquiry 810 to include the identification information, and transmit the healthcare claims attachment inquiry 810 back to comparison module 837. A person of ordinary skill in the art, however, will understand from the present invention the numerous ways that the identifying symbol may be interpreted to acquire the necessary identification information.

The identification information, along with healthcare claims attachment inquiry 810, may be routed to an acquisition module 838. Acquisition module 838 may use the identification information to locate and retrieve the content data requested in healthcare claims attachment inquiry 810. In some instances, comparison module 837 may convert a portion of the identifying information into another format in order to retrieve the content data requested. This portion may include, but not be limited to, the identifying symbol and identification message.

In one example, acquisition module 838 may route healthcare claims attachment inquiry 810 with identification information to data store 820. Data store 820 may interpret the identification message, locate the requested content data, and amend the healthcare claims attachment inquiry 810 with the content data corresponding to the identification message. Data store 820 may then route the amended healthcare claims attachment inquiry 810 back to acquisition module 838. In another example, acquisition module 838 may transmit the identification message along with additional identifying information to data store 820 and copy the corresponding content data from data store 820. In still another example, acquisition module 838 may receive the identification message along with additional information identifying the location of the corresponding content data back from data store 820.

Some healthcare claim attachment inquiries 810 may request content that cannot be located. For example, the identifying symbol may not be identified by rules module 860 criteria or the content data may not be located on an available data source 820. As a result, in accordance with the present invention, healthcare claims attachment inquiry 810 may be directed to a worklist module 840, where each data request 815 may be stored on a worklist 842 as one or more work items 844. As described previously, rules module 860 may describe an association between the identifying symbols and a corresponding worklist 842. This association may provide routing instructions for processing module 830 to place each data request 815 in an appropriate worklist 842 as work item 844. A user may access work items 844 to designate the content data or content data location. This designation may prompt transmission of the content data, or content data location, to processing module 830 through acquisition module 838.

Accordingly, and as discussed previously, acquisition module 837 may convert the content data into a standard format. This conversion prompts healthcare claims attachment inquiries 810 with content data, or content data locations, to be routed to a response module 850 or packaging module 870. These modules prepare the completed healthcare claims attachment inquiries 810 for transmission to requestor 805. Alternatively, acquisition module 838 may be operably connected to tracking module 836. After conversion, acquisition module 838 may route healthcare claims attachment inquiry 810, with attached content data or with the location of the content data, to tracking module 836 for storage. Tracking module 836 may monitor one or more healthcare claims attachment inquiries 810, related to a single healthcare claim, until all healthcare claims attachment inquiries 810 have been fulfilled. At that point, tracking module 836 may route all related healthcare claims attachment inquiries 810 to either response module 850 or packaging module 870 to complete the claims attachment transaction.

In another aspect, the process required to retrieve content data not automatedly retrieved may be captured by update module 880. This function provides a level of intelligence to healthcare system 800 that, over time, will reduce significantly the quantity of healthcare claims attachment inquiries 810 routed to worklist 742. For example, update module 880 may be operably connected to rules module 860. Thus, an acquisition of content data may prompt update module 880 to create a new criteria, stored within rules module 860, that reflects the manual steps necessary to retrieve the content data. In another alternative, update module 880 may acquire new process parameters from acquisition module 838. These new parameters may reflect a change to a stored content data criteria that would require that criteria within rules module 860 to be updated.

Figure 9:
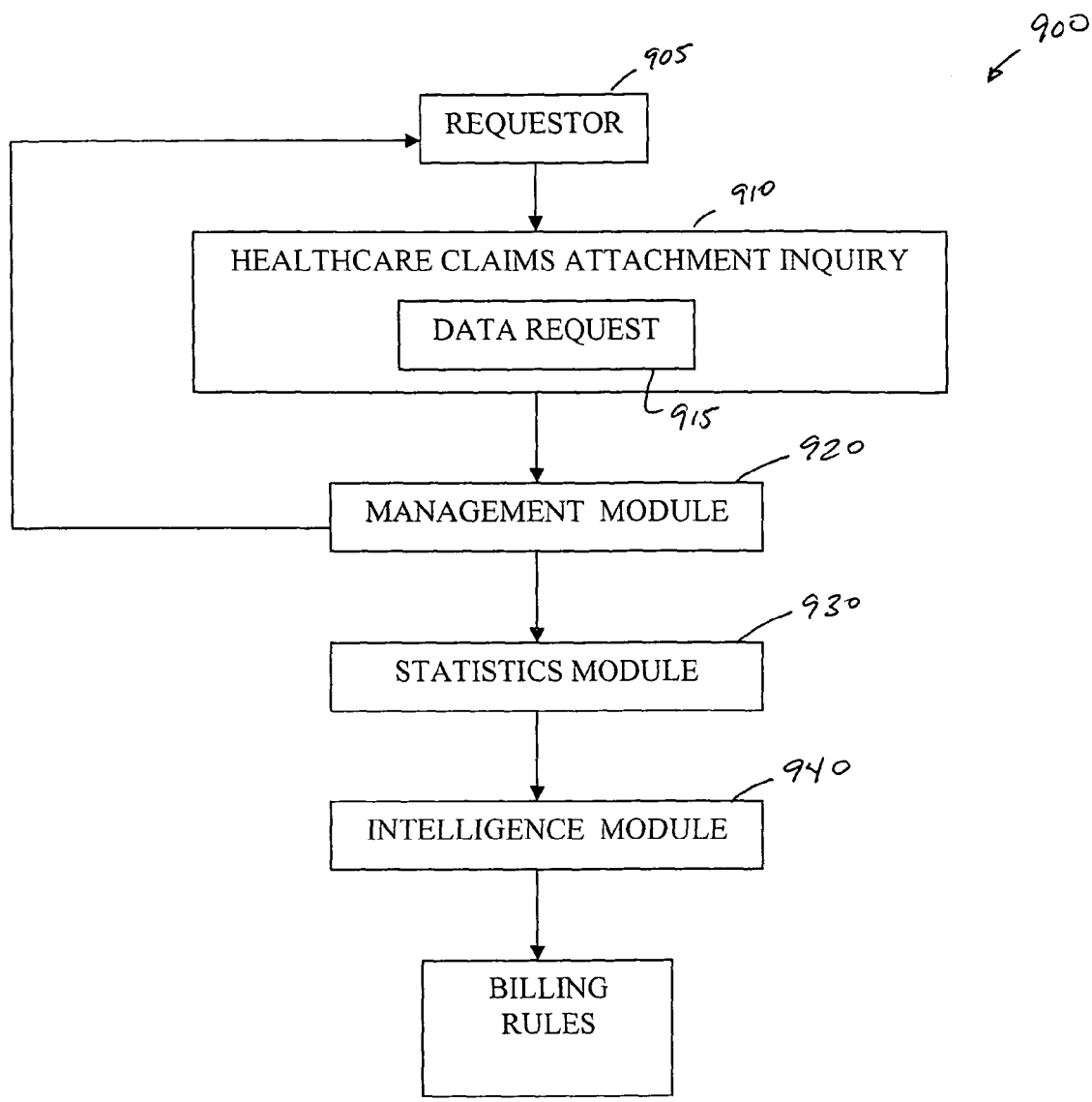
FIG. 9 is a block diagram showing an embodiment of the present invention for managing the exchange of information between healthcare systems.

This intelligence improves the healthcare system functionality by limiting the extent of user interaction required to respond to healthcare data inquiries. Further, the system just described provides an automated mechanism for receiving and processing requests for information, while also tracking and monitoring the status of healthcare data inquiries. Accordingly, FIG. 9 illustrates another embodiment of the present invention that provides further functionality.

In this embodiment, requestor 905 transmits one or more healthcare claims attachment inquiries 910 having one or more data requests 915. A management module 920 processes the one or more healthcare claims attachment inquiries 910 to produce a response that provides requester 905 with information necessary to complete a healthcare transaction. Management module 920 may determine, as discussed in the embodiments above, the content data requested by healthcare claims attachment inquiry 910. Similarly, the content data may be acquired and incorporated into a standardized response that is transmitted from management module 920 to requestor 905.

The plurality of standardized responses resulting from the one or more healthcare claims attachment inquiries 910 may produce valuable operational and management data. Accordingly, this data may be captured by a statistics module 930 operably connected to management module 920. Statistics module 930 may provide for the storage of statistical data that may include, but not be limited to, turnaround time, volume, and percent of automated responses. Additionally, the statistical data may include, but not be limited to, volume and percent of requests by type, by content, by data store, by procedure, by diagnosis, by requestor, and any combination thereof. This storage may consist of, for example, a database.

An evaluation of the statistical data may identify opportunities for changes to the various methods used to complete a healthcare data inquiry. Consequently, this evaluation may be completed by an intelligence module 940, operably connected to statistics module 930. Intelligence module 940 may contain criteria that evaluates the statistical data to provide changes to a healthcare system's various processing rules. For example, intelligence module 940 may periodically, or continuously, communicate with statistics module 930 to acquire statistical data. This statistical data may show that a specific content data is required on all healthcare claims. Accordingly, intelligence module 940 may contact a healthcare provider and update the provider's claims billing rules to examine all outgoing claims for that specific content data. Thus, every claim leaving an updated provider's system should have the specific content data.

Importantly, an intelligent system, as just described, may provide useful benefits to the healthcare system. The system would improve the claims adjudication process by reducing the need for many common healthcare data inquiries. This reduction would lower overhead costs by reducing or eliminating the incidence of submission of multiple claims attachment inquiries for any single claims. The reduction in claims attachment inquiries would increase the claims adjudication time allow health plans to provide payments to healthcare providers in a timely manner.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A system for handling one or more healthcare data inquiry requiring content data, the system comprising:
   a processing module operating on a processor that is configured to:
      receives a healthcare data inquiry from a requestor in a first standard healthcare data format, said healthcare data inquiry including at least one request for content data
      automatically determines at least one data element of the requested content data;
      determine if the at least one data element is available at a data store, and if the at least one data element is available, acquire the at least one data element from the data store;
   a worklist module operating on the processor and in communication with said processing module, said worklist module configured to:
      store one or more work items created by the processing module, when the at least one data element is available, wherein the one or more work items comprise an identification of the unavailable data element and a location of the unavailable data element;
      present the one or more work items on a graphical display; and
      receive from a user at least one data element identified by the one or more presented work items; and
   a response module operating on the processor and in communication with said processing module and said worklist module, the response module configured to:
      receive at least one acquired data element from the processing module; and
      receive at least one retrieved data element from the worklist module;
      format the acquired data element and the retrieved data element into a second standard healthcare data format; and
      send the formatted data elements to the requester.

2. A system according to claim 1, wherein said worklist module develops work items that include said at least one request for one or more content data.

3. A system according to claim 2, wherein said response module sends said data elements in response to a command generated by a user in response to said work items.

4. A system for responding to a healthcare data inquiry for content data from one or more data stores having one or more data elements stored therein, the system comprising:
   a rules module operating on a processor and that comprises one or more criteria for interpreting content data requests;
   a processing module operating on the processor and in communication with said rules module, said processing module configured to:
      receives a healthcare data inquiry, including a request for content data;
      compares the received request to said one or more criteria to identify at least one data element required by the requested content data;
      retrieves the at least one data element from one or more data stores comprising the at least one data element;
      wherein, if a data element is not available from the data stores, the processing module identifies a locally unavailable data element and a location for retrieval of the locally unavailable data element;
      cause an identification of the locally unavailable data element to be presented to a user; and
      receive the locally unavailable data element from the user;
   a response module operating on the processor and in communication with said processing module, said response module configured to sends the at least one data element retrieved from the data stores and the locally unavailable data element to a requester in a standard healthcare data inquiry format; and
   a statistics module operating on the computer processor and in communication with the processing module, the statistics module configured to collect statistics associated with the received healthcare data inquiries.

5. A system according to claim 4, further comprising a worklist module operating on the processor and working with the processing module, the worklist module configured to:
- creates one or more work items that identify the locally unavailable data element and the location; and
- presents the work item to a user for retrieval of the locally unavailable data element.

6. A system according to claim 4, wherein said healthcare data inquiry is a healthcare claims attachment inquiry and said rules module, said processing module and said response module are adapted to handle said healthcare claims attachment inquiry.

7. A system according to claim 4, wherein said healthcare data inquiry is a healthcare authorization attachment inquiry and said rules module, said processing module and said response module are adapted to handle said healthcare authorization attachment inquiry.

8. A system for automatically retrieving content data for a healthcare claim from one or more data stores having one or more data elements stored therein, the system comprising:
- a receiver module operating on a computer processor, the receiver module configured to receives a healthcare data inquiry from a requestor, said healthcare data inquiry including a request for content data;
- a rules module operating on the computer processor, the rules module comprising one or more criteria for interpreting various healthcare data inquiries,
- a comparison module operating on the computer processor and in communication with said receiver module and said rules module, said comparison module configured to:
  - compares said healthcare data inquiry to said rules to identify one or more data elements associated with said content data; and
  - determine which of the one or more data stores includes said one or more data elements;
- an acquisition module operating on the computer processor in communication with said comparison module and the one or more data stores, said acquisition module configured to acquire said identified one or more data elements;
- a worklist module operating on the computer processor, the worklist module configured to:
  - creates a work item including an identification and a location of a data element that was not retrieved by the acquisition module from the one or more data stores;
  - cause the work item to be presented to a user; and
  - receive a retrieved data element from the user;
- a response module operating on the computer processor in communication with said acquisition module and said worklist module, said response module configured to:
  - receive the acquired data elements from the acquisition module;
  - receive the retrieved data elements from the worklist module; and
  - send said one or more data elements to said requestor in a standard format; and
- a statistics module operating on the computer processor and in communication with the processing module, said statistics module configured to collects statistics associated with the received healthcare data inquiries.

9. A system according to claim 8, further comprising a notification module operating on the computer processor in communication with said receiver module, wherein said notification module generates a billing system notification.

10. A system according to claim 8, further comprising a tracking module operating on the computer processor in communication with said receiver module and said comparison module, where said tracking module generates a tracking record associated with said healthcare data inquiry.

11. A system according to claim 8, further comprising an update module operating on the computer processor that updates said one or more rules with information learned during an acquisition of a particular data element.

12. A system according to claim 8, further comprising a packaging module operating on the computer processor in communication with said response module, wherein said packaging module formats the retrieved one or more data elements into a standard healthcare data format and bundles a plurality of said one or more data elements for delivery to said requester.

13. A system according to claim 8, further comprising an intelligent learning module operating on the computer processor in communication with said statistics module, the intelligent learning module analyzes said statistics and modifies the one or more criteria of the rules module, in response to the analyzed statistics.

14. A system according to claim 8, wherein said standard format includes an X12N 275 healthcare claims standard.

15. A system according to claim 8, wherein said healthcare data inquiry is a healthcare authorization attachment inquiry.

16. A method of responding to a healthcare data inquiry, the method comprising:
- receiving with a processor a healthcare data inquiry from a requester, said healthcare data inquiry including a request for content data;
- automatedly determining with the processor at least one data element of the requested content data by applying at least one criteria including one or more rules for interpreting a request for content data;
- automatedly determining with the processor a location of the at least one available data element from a plurality of data stores;
- automatically determining with the processor, at least one unavailable data element, not found in the plurality of data stores;
- presenting an identification of the unavailable data element;
- receiving, with the processor, the at least one unavailable data element, retrieved from outside of the plurality of data stores;
- retrieving with the processor said the at least one available data element from the plurality of data stores;
- formatting with the processor the at least one available data element and at least one unavailable data element into a claims attachment in a predetermined format;
- transmitting said claims attachment to said requestor;
- monitoring, with the processor, statistics regarding a plurality of healthcare data inquiries from the requester;
- analyzing the statistics with the processor; and
- modifying the one or more rules based on the analyzed statistics.

17. A method according to claim 16, wherein said receiving step involves receiving said request from a third party payer.

18. A method according to claim 16, wherein said receiving step involves receiving said request from a claims financial system.

19. A method according to claim 16, wherein said receiving step involves receiving said request from an Electronic Data Interchange (EDI) system.

20. A method according to claim 16, further comprising creating with the processor a tracking record associated with said healthcare data inquiry.

21. A method according to claim 16, further comprising generating with the processor a billing system notification, said notification indicating receipt of said healthcare data inquiry.

22. A method according to claim 16, further comprising:
   storing said healthcare data inquiry in a first database; and
   retrieving said healthcare data inquiry from said first database.

23. A method according to claim 16, further comprising packaging a plurality of the at least one data element for delivery to said requestor.

24. A method according to claim 16, wherein said predetermined format includes an X12N 275 healthcare claims standard.

25. A non-transitory computer readable medium having computer-executable instructions for implementing a method of managing the exchange of information between healthcare systems, the instructions comprising:
   a first set of instructions for receiving a healthcare data inquiry from a requestor, said healthcare data inquiry including a request for content data;
   a second set of instructions for automatedly determining one or more data elements in the requested content data using a criteria including one or more rules for interpreting a variety of content data;
   a third set of instructions for automatedly determining a location of said one or more data elements amongst one or more data stores;
   a fourth set of instructions for retrieving said one or more data elements from said one or more data stores;
   a fifth set of instructions for formatting said one or more data elements into a claims attachment in a predetermined format;
   a sixth set of instructions for transmitting said claims attachment to said requestor; and
   a seventh set of instructions for monitoring a plurality of received healthcare data inquiries and modifying the one or more rules in response to the monitored healthcare data inquiries.

26. A computer readable medium according to claim 25, said instructions including an eighth set of instructions for creating a tracking record associated with said healthcare data inquiry.

27. A computer readable medium according to claim 25, said instructions including an eighth set of instructions for generating a billing system notification, said notification indicating receipt of said healthcare data inquiry.

28. A computer readable medium according to claim 25, said instructions including:
   an eighth set of instructions for storing said healthcare data inquiry in a first database; and
   a ninth set of instructions for retrieving said healthcare data inquiry from said first database.

29. A computer readable medium according to claim 25, said instructions further comprising an eighth set of instructions for packaging a plurality of said one or more data elements for delivery to said requestor.

* * * * *